United States Patent [19]

Merrill

[11] Patent Number: 4,884,577
[45] Date of Patent: Dec. 5, 1989

[54] PROCESS AND APPARATUS FOR MEASURING BLOOD VISCOSITY DIRECTLY AND RAPIDLY

[76] Inventor: Edward W. Merrill, 90 Somerset St., Belmont, Mass. 02178

[21] Appl. No.: 750,897

[22] Filed: Jul. 1, 1985

Related U.S. Application Data

[63] Continuation of Ser. No. 666,653, Oct. 31, 1984, abandoned.

[51] Int. Cl.$^4$ ............................................. A01B 10/00
[52] U.S. Cl. ........................................ 128/637; 73/57
[58] Field of Search ...................... 128/637; 73/55, 57

[56] References Cited

U.S. PATENT DOCUMENTS

| | | | |
|---|---|---|---|
| 3,071,961 | 1/1963 | Heigl et al. | 73/55 |
| 3,194,057 | 7/1965 | Richard | 73/55 |
| 3,720,097 | 3/1973 | Kron | 73/55 |
| 3,908,441 | 9/1975 | Virloget | 73/55 |
| 4,207,870 | 6/1980 | Eldridge | 128/766 |
| 4,367,754 | 1/1983 | Akhavi | 128/763 |

OTHER PUBLICATIONS

Walker et al., Med. & Biol. Engr., vol. 14, No. 5, Sep. 1976, pp. 551–557.
Gilinson et al., Trans. of the Soc. of Rheology, vol. VII, 1963, pp. 319–331.
Bowlt, Physics Ed., vol. 10, No. 2, Mar. 1975, pp. 102–103.
Shvestka, Polymer Sci. (USSR), vol. 16, No. 1, 1974, pp. 264–268.
Swank et al., Review of Sci. Instruments, vol. 25, No. 10, Oct. 1954, pp. 1020–1022.

*Primary Examiner*—Kyle L. Howell
*Assistant Examiner*—John C. Hanley
*Attorney, Agent, or Firm*—Paul J. Cook

[57] ABSTRACT

Apparatus for rapidly measuring blood viscosity including a hollow column of narrow bore in fluid communication with a chamber containing a porous bed and means for measuring blood flow rate within the column. The specific permeability of the bed and the pressure gradient are selected so that in combination they result in an equivalent average wall shear stress of about 1 dyn/cm$^2$ or less.

7 Claims, 2 Drawing Sheets

PROCESS AND APPARATUS FOR MEASURING BLOOD VISCOSITY DIRECTLY AND RAPIDLY

This is a continuation of co-pending application Ser. No. 666,653 filed on Oct. 31, 1984 now abandoned.

BACKGROUND OF THE INVENTION

This invention relates to the process and apparatus for measuring the resistance to flow of a patient's blood under conditions approximating the microcirculatory vessels. Resistance to flow of blood is measured as an apparent viscosity, the flow taking place through a porous bed. The apparent viscosity of blood decreases from indefinitely large values near zero flow rates to an asymptotic value of the order of 3 to 5 centipoise over wall shear stresses of the order of 5 dyn/cm$^2$.

It is important to provide a screening test for large patient populations to determine a patient's blood shear-rate dependent viscosity in order to determine whether further analysis is required to measure the factors in the blood that affect blood viscosity. The non-Newtonian behavior of blood viscosity is determined by hematocrit (red cell volume percent) and macromolecular concentrations, primarily fibrinogen which in turn determines the ease of blood flow through microvasculature of the body and this varies widely from patient to patient. When blood flow is reduced during the normal course of passive and active distribution control, red blood cells and fibrinogen act to form red blood cell clusters or rouleaux which can cause undesirable stoppage of microvascular flow. Rouleaux require certain levels of fluid shear stress to cause their breakup. When the blood's fibrinogen is high, fluid shear stress required to break up the rouleaux or to restart microvascular stoppage is commensurately higher and sufficient energy may not be available from the normal proximal flow. These aggregate phenomena can aggravate or promote local tissue anoxia, cerebral, myocardial or other organ infarctions and/or deep vein thrombosis. Aggregating phenomena also can occur due to stasis in a blood vessel brought about by surgical procedures. The aggregating tendency of red blood cells is a manifestation of attraction between their surfaces which can also be detected as an increase in sliding friction, if the cells are forced to move past each other slowly. These are the conditions easily attained in flow in the microcirculatory vessels: arterioles, capillaries, the venules, especially in the ever dividing channels of the arteriolar circuit and ever converging channels of the venular circuit. Typical inner diameters of these vessels range from 200 $\mu$m to 8 $\mu$m, and probably most of the arterio-venous blood pressure drop occurs in arterioles and capillaries having diameters less than 50 $\mu$m. Accordingly, it would be highly desirable to provide a determination of a patient's apparent blood viscosity under conditions relevant to flow in his microcirculatory vessels which is accurate, reproducible and simple to operate so that a patient can be appropriately diagnosed and treated in order to minimize or avoid the physiological risks of cellular aggregation.

Many presently available techniques for measuring blood viscosity are really aimed at measuring the endpoint of surface-induced blood coagulation, the gel point, whereas in the described invention complications of coagulation are intentionally avoided. For example, U.S. Pat. No. 3,587,295 discloses a procedure for measuring the coagulation characteristics of blood by subjecting the blood to mechanical energy and measuring the intensity of the energy transmitted to the blood which then is correlated with the coagulation characteristics of the blood. U.S. Pat. No. 3,053,078 also utilizes an indirect methods whereby a rotatable means is inserted into the blood and rotated at a constant velocity and the resistance to rotation then is measured and correlated with the coagulation characteristics of the blood. U.S. Pat. No. 3,911,728 discloses a process for measuring blood viscosity by placing a blood sample and a confined gas in a tube having a narrow cross-section and reciprocally moving the blood through the narrow cross-section. The gas pressure variations due to compression of the gas are measured and then correlated with viscosity. Other indirect means for measuring physical characteristics of blood are shown in U.S. Pat. Nos. 3,918,908; 3,967,934; 4,187,462 and 4,202,204. Since the means for measuring blood viscosity as disclosed in the cited patents are indirect, errors are introduced which render the results for less reliable than could be obtained with a direct blood viscosity measurement.

When the viscosity of anticoagulated blood is determined by conventional capillary viscometers, cone-and-plate viscometers, or cylindrical viscometers, the flow rates or shear rates are usually so high that the sliding friction and aggregating effects are obliterated, and the viscosity of the blood determined under such conditions appears to be both Newtonian (independent of flow rate) and dependent only on volume percent red cells (hematocrit). Consequently the clinician has often relied on hematocrit reading as a guide to probable blood viscosity level, unaware of the fact that macromolecular plasma concentrations, especially of fibrinogen, can greatly increase the level of apparent viscosity that will be relevant in microcirculating flows.

SUMMARY OF THE INVENTION

In accordance with this invention, the apparent viscosity of blood is measured under conditions analogous to slow flow in the microcirculatory vessels by means of a porous bed, having pore dimensions comparable to the inner diameters of the microcirculatory vessels, whereby the sliding frictional effects, divisions of the flow and recombination of flow found in the living microcirculatory vessels can be approximated, and at the same time the flow through the bed is limited to a rate such that, in combination with the small pore size, the average wall shear stress is 1 dyn/cm$^2$ or less.

The apparatus includes a hollow transparent column in fluid communication with a chamber containing a porous bed. The porosity can be created in a variety of ways, for example, by packing fine spherical beads into a column, by synthesis of macroreticular networks from reagents like divinyl benzene, or by phase separation of polyolefins. All that is required is that the porosity be reasonably uniform throughout the bed, to minimize channeling, and that the pore diameters fall in the range of approximately 10 $\mu$m to 200 $\mu$m, preferably from 10 $\mu$m to 50 $\mu$m. Furthermore, reproducibility from bed to bed is obviously desirable.

In use, blood is withdrawn from a patient and injected into the apparatus of this invention so that it permeates the porous bed and fills at least a portion of the hollow column. The blood sample then is allowed to pass through the porous bed and the flow rate of the blood in the column is measured. The lower the flow rate the more viscous the blood sample.

The flow condition created by the apparatus of this invention yields a viscosity value by measurement of the flow rate through a porous bed by the application of Darcy's Law:

$$Q/A = (B_o/\mu)(\Delta P/L)$$

wherein
Q = volumetric flow rate, cm$^3$/sec
A = total area of bed normal to flow, cm$^2$ (so that Q/A is the approach velocity to the bed, cm/sec)
$B_o$ = Darcy specific permeability, cm$^2$
$\mu$ = viscosity of liquid, in poise (1 poise = 1 dyn-sec/cm$^2$)
L = total length of bed in direction of flow, cm
$\Delta P$ = pressure difference across bed, dyn/cm$^2$ In the device of this invention, the pressure difference is generated by a column of blood of average height $\bar{h}$ cm above the outlet, so that:

$$\Delta P = \rho g \bar{h}$$

where
$\rho$ = density of liquid (blood), g/cm$^3$ (about 1.0)
g = gravitational acceleration, 980 cm/sec$^2$ As practiced, it is convenient to measure volumetric flow rate Q by timing the fall of the upper meniscus of blood from a height $h_o$ to a final height $h_f$. Thus $\bar{h} = (h_o + h_f)/2$.

The meniscus moves downward in a capillary tube of about 1 mm inside diameter, thus of cross-sectional areas $a_{cap} \approx 0.01$ cm$^2$. Thus $$Q = (h_o - h_f) a_{cap.}/\Delta t$$

where $\Delta t$ = time interval, seconds, for meniscus to fall from $h_o$ to $h_f$, typically about 1 cm.

It is found that the specific permeability of the bed should be about $6 \times 10^{-8}$ cm$^2$, corresponding to 6 Darcy. [1 Darcy = 1(cm$^3$)(centipoise)(cm$^{-1}$)(sec$^{-1}$)(atm$^{-1}$)].

The equivalent radius of a capillary tube $r_e$ having the same Q/A under the same pressure gradient $\Delta P/L$ is given by the relation $$r_e^2 = 8B_o$$

For $B_o = 6 \times 10^{-8}$ cm$^2$, $r_e = 7 \times 10^{-4}$ cm = 7 $\mu$m

The equivalent shear stress $\tau_e$ in the equivalent capillary is defined as:

$$\tau_e = (\Delta P/L)(r_w/2) \text{dyn/cm}^2$$

so $\tau_e = (\Delta P/L)\sqrt{2B_o}$ and under the preferred conditions ($\bar{h} = 5$, L = 3, assuming $r_w = 7 \times 10^{-4}$,) $\tau_e \approx 0.6$ dyn/cm$^2$.

The equivalent wall shear *rate* for the flow of a Newtonian liquid through the equivalent capillary is calculated as:

$$\dot{\gamma}_e = \tau_e/\mu$$

For blood plasma, $\mu \approx 0.01$ poise and thus $\dot{\gamma} \approx 60$ sec$^{-1}$ for the above example, but for blood, at low flow rates, its non-Newtonian properties could easily result in an effective $\mu$ of 0.10 or higher, corresponding to $\dot{\gamma}_e$ of about 6 sec$^{-1}$ or less.

As will be seen, it is particularly convenient to make the hollow column diameter 1/10th or less the diameter of the porous bed; for example 1 mm column diameter with a 1 cm bed diameter. As a consequence of the difference in area ratios by a factor of 100 thereby resulting, the approach velocity to the porous bed, which is inconveniently low in value, is reflected in a flow velocity through the hollow column 100-fold greater, leading to meniscus movements measurable in the range of centimeters per minute.

It is not essential to use freshly drawn blood from a patient. Blood can be drawn into anticoagulant sample tubes and tested subsequently in the device of this invention. However it is believed that greatest accuracy is achieved when blood is drawn directly from the patient's vein and immediately introduced into this device. The device is preferably pre-warmed to body temperature, 37° C. One of the outstanding advantages is the speed with which a determination can be made. The end point reading can easily be obtained within 180 seconds from venopuncture, before coagulation begins. The ability to carry out the test so rapidly means that problems of platelet aggregation, possible changes in red cell stiffness due to storage or lack of dextrose, and other potential artifacts can be avoided. Furthermore, the temperature of the blood will necessarily be close to that of the body, 37° C., and thus, the viscosity measured will correspond to usual physiological temperatures in the microvasculature.

DESCRIPTION OF SPECIFIC EMBODIMENTS

Figure 1:
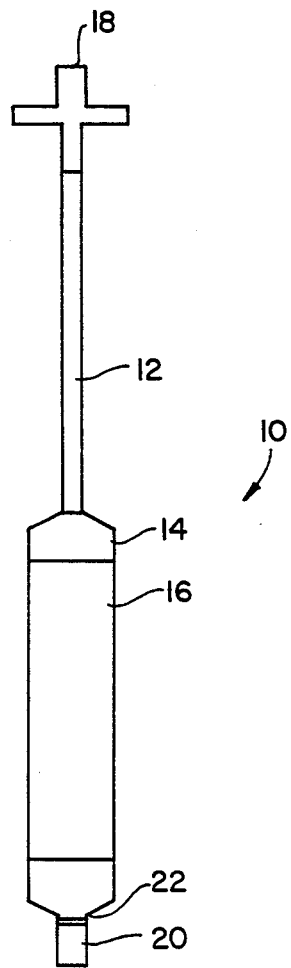
FIG. 1 is a side view of the apparatus of this invention including a vent cap.

Referring to FIG. 1, the apparatus of this invention 10 includes a hollow column 12, and a chamber 14 which chamber contains a porous bed 16. A blood sample inlet 18 is provided at the top of the column 12 and a hydrophobic vent cap 20 is fitted over a blood outlet 22 at the lower end of chamber 14. A blood sample, preferably, but not necessarily taken immediately beforehand from the patient into a syringe by venipuncture, is introduced through inlet 18 and is allowed to flow through column 12 progressively filling chamber 14 while air is expelled through hydrophobic vent cap 20. The hydrophobic vent cap 20 prevents passage of blood therethrough so that, after the chamber 14 and column 12 are filled with blood, the vent cap 20 can be removed in order to initiate blood flow through the chamber 16 and the column 12.

Figures 2, 3:
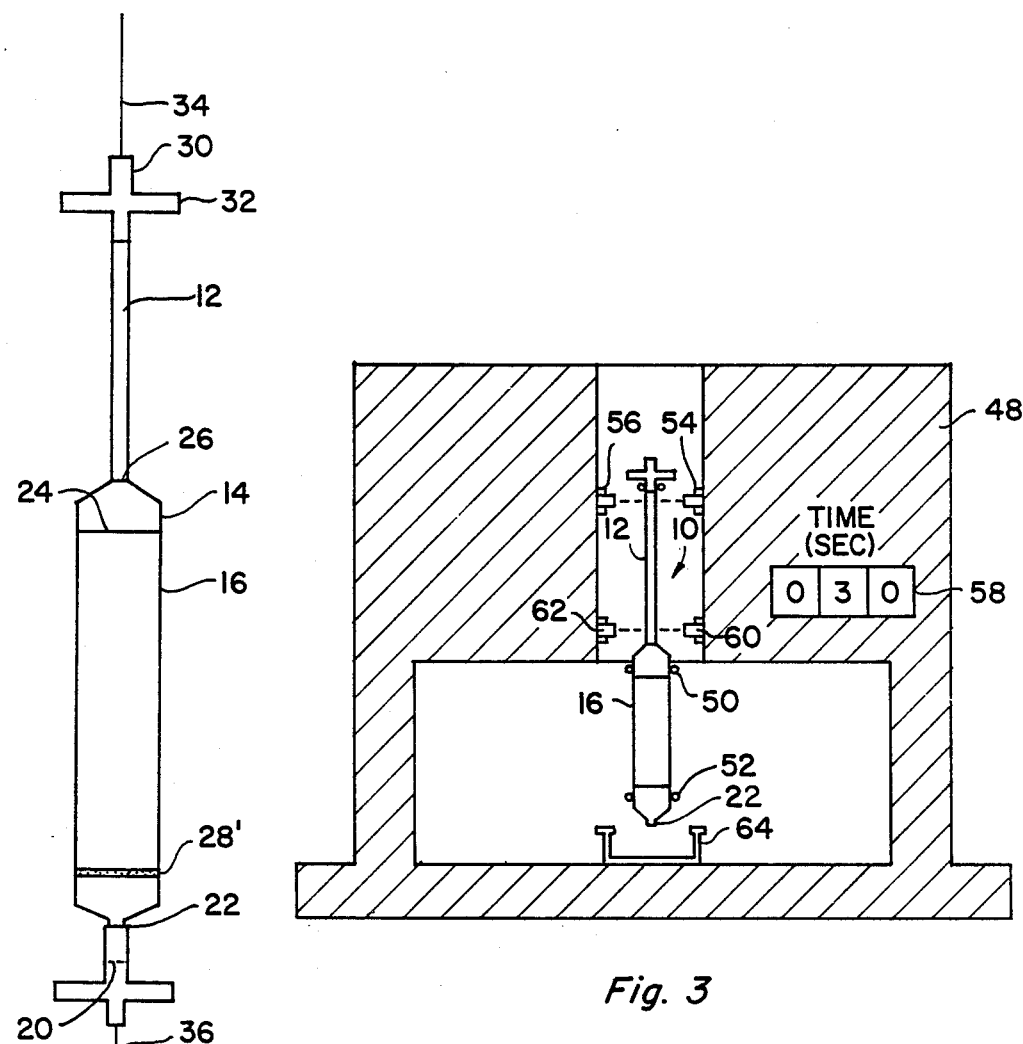
FIG. 2 is a side view of an embodiment of this invention including a vacuum tube.
FIG. 3 is a partial cross-sectional view showing measurement of blood flow in accordance with this invention.

Referring to FIG. 2, an alternative embodiment is shown which includes means for taking a blood sample directly from the patient and introducing it into the apparatus of this invention. The apparatus includes a column 12, a chamber 14, and a porous bed 16. As for the device shown in FIG. 2, it is preferred that the top surface 24 of the porous bed 16 be spaced apart from the column outlet 26 in order to promote even flow across the horizontal cross-sectional areas of the packed bed 16. In addition, it is preferred that the packed bed 16 be spaced apart from the chamber outlet 22 such as by means of a screen 28 in order to promote even flow across the horizontal cross-section of the packed bed 16.

Attached to the top of column 12 is a venipuncture device 30 which includes a holder 32 and a needle 34.

Venipuncture is accomplished in the usual way by grasping piece 32 so as to introduce needle 34 into the vein of a patient. Blood is introduced rapidly into the column 12 and the chamber 16 when needle 36 is inserted through seal 38 into tube 40 which is maintained under vacuum. The vacuum in tube 40 will cause blood eventually to flow through column 12, chamber 16 and into vacuum tube 40, unless hydrophobic vent cap 20 is interposed. In that case, the blood is stopped at that place.

Referring to FIG. 3, the blood viscometer 10 is placed within fixture 48 by means of clamps 50 and 52 after chamber 16 and column 12 have been filled with a patient's blood. Preferably, fixture 48 is thermostatically controlled at a constant temperature, preferably 37° C., in order to maintain the viscometer and blood contained therein at constant temperature. The hydrophobic vent cap (not shown) is removed from chamber outlet 22 so that blood flows by gravity down column 12, down chamber 16 so that the air-blood interfaces pass first between light emitting diode 54 and photodiode 56 which starts a conventional clock mechanism (not shown) having an associated time readout 58. As the air-blood interface passes downwardly through column 12, it passes a second set comprising a light emitting diode 60 and a photodiode 62 which causes the clock mechanism to stop. The operator then can easily read the elapsed time between the top set of diodes 54 and 56 and the bottom set of diodes 60 and 62 from the time readout 58. The blood passing through column 12 and chamber 16 flows into container 64. Since the blood flow rate through the column 12 depends upon its viscosity, the operator can easily determine the tendency of a particular patient to have abnormal microcirculation by comparing the time readout with a previously established standard.

The material utilized in the porous bed should not promote blood hemolysis and should allow blood permeation such that the average wall shear stress with blood is about 1 dyn/cm$^2$ or less sec$^{-1}$. Suitable average pore sizes are between about 10 $\mu$m and about 200 $\mu$m, preferably between about 10 $\mu$m and about 50 $\mu$m. The bed should have a specific Darcy permeability of not more than 50 Darcy units (50×10$^{-8}$ cm$^2$), preferably less than 10 Darcy units. Representative suitable particles include glass beads, preferably silane treated; polystyrene beads; polyethylene particles, and beds formed by sintering or related processes, for example, rods of sintered porous glass and analogous products produced by sintering granular plastic such as polyethylene, polypropylene, polyvinyl chloride, etc.

Generally, suitable bed thicknesses are between about 1 cm and about 10 cm, preferably between about 2 cm and about 4 cm and bed diameters are 0.5 to 2 cm, preferably 0.75 to 1.5 cm.

It is desirable that the apparatus of this invention does not require excessively large blood samples to be taken from the patient for testing. Therefore, the preferred bed sizes are set forth above while preferred column dimensions are of a height between about 1 cm and about 5 cm, preferably between about 2 cm and about 3 cm and an inside diameter between about 0.5 mm and about 2 mm, preferably around 1 mm and preferably not more than 1/10 the diameter of the porous bead.

It is obvious that the apparatus of FIG. 1 or of FIG. 2 could be initially filled with blood in the reverse direction to that shown, by placing hydrophobic vent cap 20 on opening 18 and introducing blood through opening 22.

In this case readout apparatus of FIG. 3 would be modified by fixing clamps 50 and 52 on a frame having an axis of rotation slightly below the diode pair 60-62.

The frame through appropriate detent mechanism would have either of two vertical positions, differing by 180°: loading position (clamp 52 above 50, both above rotation axis), and reading position (clamp 52 under 50, both under axis of rotation) as shown in FIG. 3.

The apparatus after filling in the reverse direction is loaded into the clamps when they are in the loading position as described, thus with the chamber 14 above column 12, with hydrophobic vent 20 underneath.

The operator starts the readout by simply filling the frame to the reading position, which brings column 12 above chamber 14. Blood now drains from chamber 14 into receiver 64 as air is aspirated into column 12 through cap 20.

It is obvious that other means for measuring viscosity other than measuring blood flow rate directly can be utilized in the present invention. For example, the volume of blood in container 64 could be measured as a function of time and related to a previous standard that correlates volume with viscosity. Usually the devices will be pre-calibrated with standard fluids, for example physiologic saline solution and it will be known that, for example, the elapsed time between diodes is 6 seconds. If a sample of blood is found to take 30 seconds, its viscosity is then 30/6 or 5 times the viscosity of saline. Obviously, the standard fluid will be run in the device at the same temperature as the blood sample, preferably at or near 37° C., as explained above, for most patients.

The device can also be run at lower temperatures, for example 20° C., especially when cryoglobulinemia is suspected in the patient. If cryoglobulinemia is present, apparent blood viscosity will be drastically increased when measured at 20° C. as compared to 37° C. In such a case it would be desirable to take sufficient blood from the patient to fill two devices, and run one at 37° C. and the other at 20° C.

I claim:

1. Apparatus for measuring blood viscosity which comprises a hollow column in fluid communication with a chamber containing a porous bed having pores of a size between about 10 $\mu$m and about 200 $\mu$m, the permeability ($B_o$) of said bed, the length, L of said bed and the pressure gradient across said bed ($\Delta P/L$) being such that the average wall shear stress defined as ($\Delta P/L)\sqrt{2\,B_o}$ is about 1 dyn/cm$^2$ or less when blood is passing through said bed during the course of viscosity measurement, said hollow column having an inlet at a first end of said column and an outlet at a second end of said column and said chamber having a chamber inlet at a first end of said chamber and in fluid communication with the column outlet and a chamber outlet at a second end of said chamber to permit blood flow through said column and said chamber and means for measuring the flow rate of blood through said chamber.

2. The apparatus of claim 1 wherein said means for measuring the flow rate of blood through said chamber comprises optical means adapted to sense movement of an air-blood interface in said column.

3. The apparatus of claim 1 wherein the means for measuring the flow rate of blood through said chamber comprises a container positioned at the outlet of said chamber to collect a volume of blood passing through said chamber, said container, together with means for determining the time interval to collect said volume being adapted to provide a measurement of collected blood volume as a function of time.

4. The apparatus of claim 1 wherein the diameter of said column is one-tenth or less than the diameter of said porous bed.

5. Apparatus for withdrawing blood from a patient for the measurement of blood viscosity which comprises a hollow column in fluid communication with a chamber containing a porous bed having pores of a size between about 10 $\mu$m and about 200 $\mu$m, the permeability ($B_o$) of said bed, the length, L, of said bed and the pressure gradient across said bed ($\Delta P/L$) being such that the average wall shear stress defined as $(\Delta P/L)\sqrt{2B_o}$ is about 1 dyn/cm or less, when blood is passed through said bed, said hollow column having an inlet at a first end of said column and an outlet at a second end of said column and said chamber having a chamber inlet at a first end of said chamber and in fluid communication with the column outlet and a chamber outlet at a second end of said chamber to permit blood flow through said column and said chamber, a first hollow needle adapted to withdraw blood from a patient, said first needle being secured to said column and in fluid communication with the inlet to said column and a second hollow needle adapted to withdraw blood from said chamber and in fluid communication with the outlet of said chamber.

6. The apparatus of claim 5 wherein the diameter of said column is one-tenth or less than the diameter of said porous bed.

7. The process for measuring blood viscosity which comprises passing a blood sample sequentially through a hollow column in fluid communication with a chamber containing a porous bed, the permeability ($B_o$) of said bed, the length, L, of said bed and the pressure gradient across said bed ($\Delta P/L$) being such that the average wall shear stress defined as $(\Delta P/L)\sqrt{2B_o}$ is about 1 dyn/cm or less, said hollow column having an inlet at a first end of said column and an outlet at a second end of said column and said chamber having a chamber inlet at a first end of said chamber and in fluid communication with the column outlet and a chamber outlet at a second end of said chamber to permit blood flow through said column and said chamber, and measuring the flow rate of blood through said chamber.

* * * * *